Figure 1:
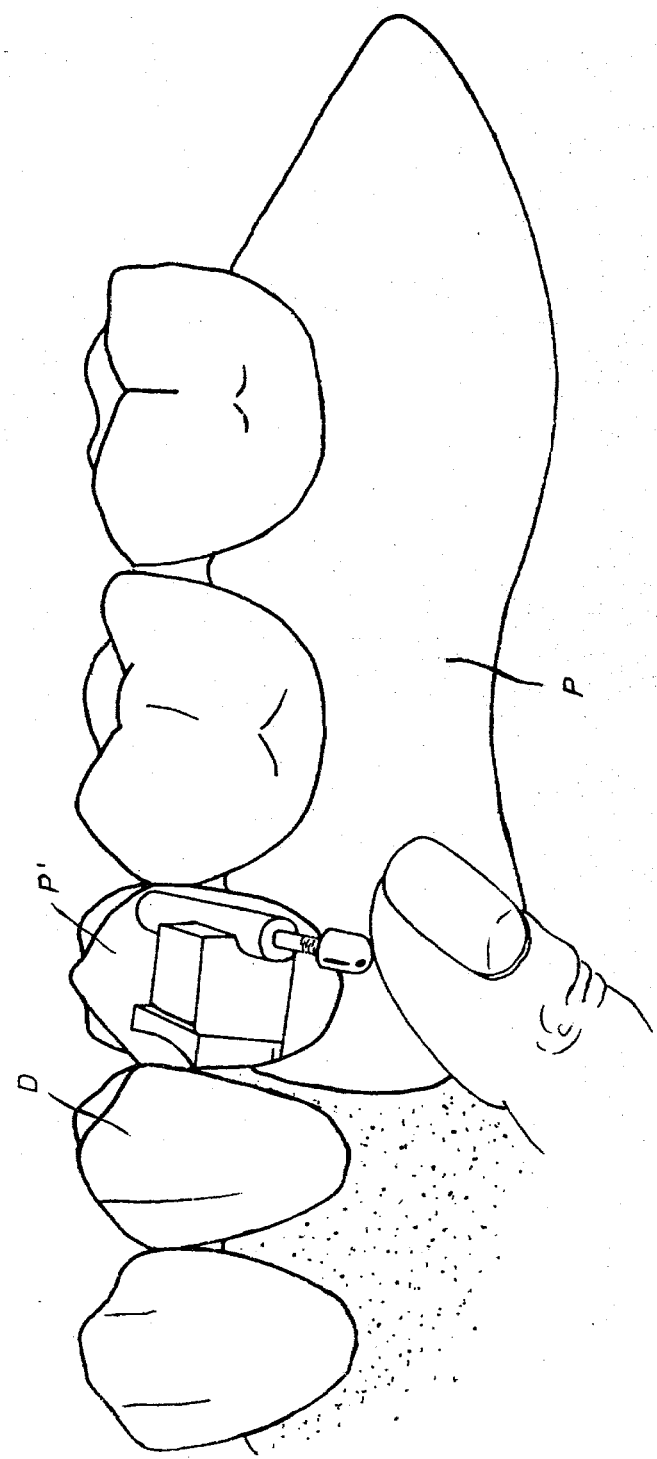

United States Patent [19]

Romagnoli

[11] 4,345,901

[45] Aug. 24, 1982

[54] DENTAL PROSTHESIS CONNECTING APPARATUS

[75] Inventor: Mario Romagnoli, Milan, Italy

[73] Assignee: Metaux Precieux S.A., Neuchatel, Switzerland

[21] Appl. No.: 145,338

[22] Filed: Apr. 30, 1980

[30] Foreign Application Priority Data

May 9, 1979 [IT] Italy ................................ 22485 A/79

[51] Int. Cl.³ ............................................. A61C 13/22
[52] U.S. Cl. ..................................... 433/172; 433/177; 403/324
[58] Field of Search ............... 433/172, 177, 178, 181, 433/182, 190, 191, 193, 194; 403/322, 324

[56] References Cited

U.S. PATENT DOCUMENTS

| | | | |
|---|---|---|---|
| 1,693,845 | 12/1928 | Kellner et al. | 433/177 |
| 3,109,617 | 11/1963 | Meyer | 403/324 |
| 3,427,718 | 2/1969 | Scott | 433/172 |
| 3,675,326 | 7/1972 | Desmarets | 433/182 |

FOREIGN PATENT DOCUMENTS 336898  9/1919  Fed. Rep. of Germany ...... 433/191
19830  7/1974  Italy ................................. 433/172

*Primary Examiner*—Gene Mancene
*Assistant Examiner*—John J. Wilson
*Attorney, Agent, or Firm*—Stevens, Davis, Miller & Mosher

[57] ABSTRACT

Connecting apparatus for removable dental prostheses comprises a frustoconical male element attached to a base and including a cylindrical transverse groove and an oblique groove. A female part is essentially composed of a block having a frustoconical cavity matching the male element so that the female part can be fitted over the male element. A tubular sleeve accommodates a sliding member which is biased axially by a spring held in place by a cap screwed on one end of the sleeve. A tip attached to a threaded section at the end of the sliding member remote from the spring makes it possible to displace the sliding member axially against the bias of the spring. When the block is fitted over the male element, a section of the sliding member is caught by the edge of the oblique groove and moved axially, then enters the transverse groove, thereby interlocking the male element and the female part.

7 Claims, 5 Drawing Figures

DENTAL PROSTHESIS CONNECTING APPARATUS

This invention relates to connecting apparatus for removable dental prostheses, and more particularly to apparatus of the type comprising a male part, normally fixed to a remaining natural tooth, a female part, normally adjoining the prosthesis and engaging the male part, and a device joining these parts to one another.

The prior art has long included proposals for fixing a body to a crown or other element made integral with a sound tooth and providing, adjacent to the prosthesis, a hollow part, the interior of which matches the body in size and shape and can be fitted over it to position the prosthesis. For example, German Pat. No. 336,898, U.S. Pat. No. 3,427,718, and Italian Pat. No. 1,007,101 all describe connecting apparatus in which the body has the shape of a pyramid or parallelepiped. According to the teaching of German Pat. No. 336,898, the prosthesis is fixed by means of a threaded pin or a screw which presses the prosthesis axially against the body, i.e., toward the jaw. In U.S. Pat. No. 3,427,718, the attachment means consist of a number of pins which slide into corresponding passages, likewise axial, with locking being achieved by lateral pressure. According to the disclosure of Italian Pat. No. 1,007,101, the part of the connecting apparatus integral with the remaining natural teeth, and forming the body fitting into a recess in the prosthesis, includes an L-shaped indentation opening out in one of the plane walls of the pyramidal body for receiving a sliding member mounted on the prothesis and biased by a spring.

In comparison with previous systems, this last-mentioned system presents the advantage of not requiring the fitting of a screw of bolt and the maneuvering of this part when the prosthesis is being fixed in place. It also avoids the wear and tear on screws or bolts which proved troublesome in earlier systems. With the system taught by the aforementioned Italian patent, it suffices to press the prosthesis onto the body integral with the remaining natural teeth, whereupon it snaps securely into place.

It has turned out in practice, however, that this system still has its shortcomings inasmuch as the pyramidal body, which must precisely match the interior of the female part of the connecting apparatus, integral with the prosthesis, may likewise be subject to wear, so that after a few manipulations, a tight grip of the prosthesis on its body is no longer ensured.

It is an object of this invention to provide an improved connecting apparatus of the type disclosed in Italian Pat. No. 1,007,101 whereby the prosthesis remains securely seated without any play, while avoiding the use of screws or other tightening elements requiring maneuvering at the time of positioning.

To this end, in the dental prosthesis connecting apparatus according to the present invention, of the type initially mentioned, the improvement comprises male and female parts of frustoconical shape, and a joining device including a sliding member mounted on the movable female part, transversely to the axis thereof, and a transverse groove in the fixed part, the sliding member engaging the groove in order to lock the two parts.

Figure 2:
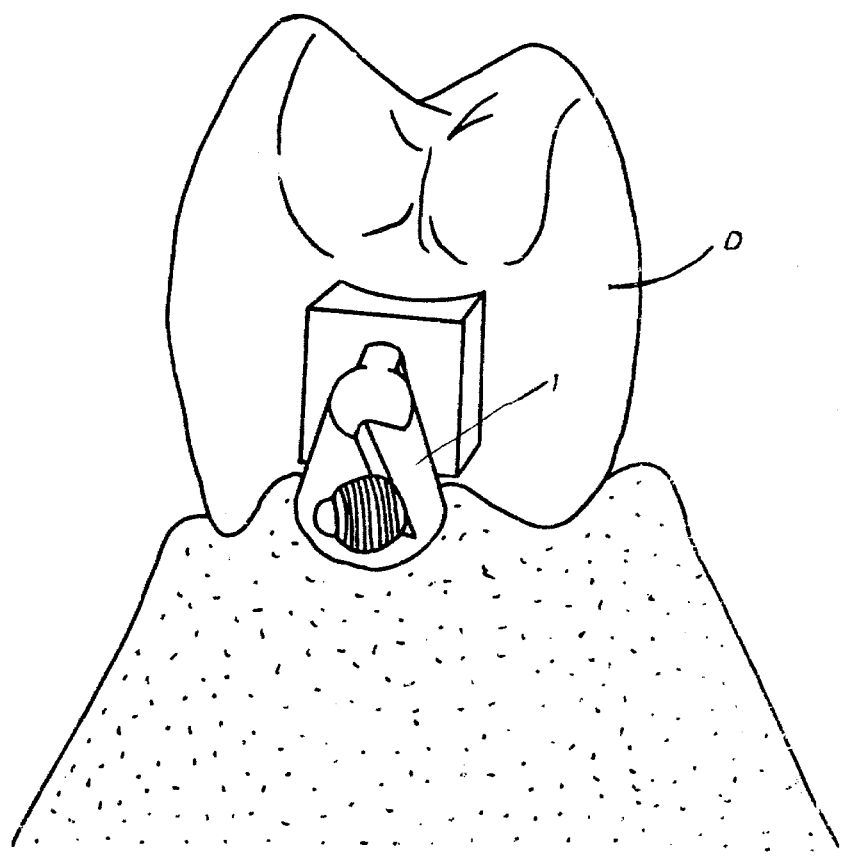
Figure 3:
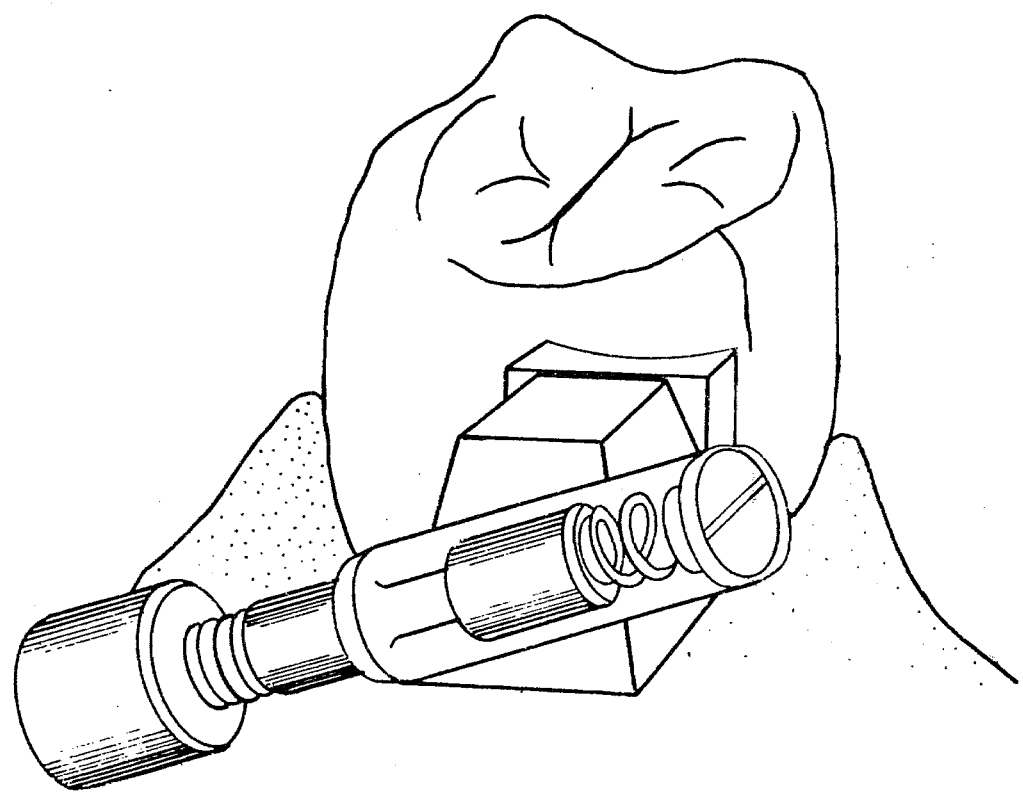
Figure 4:
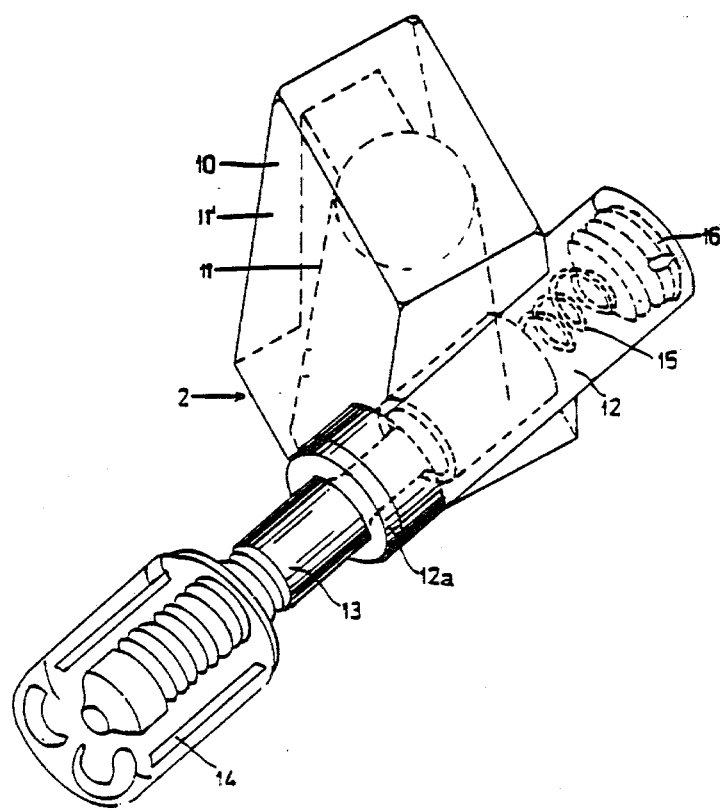
Figure 5:
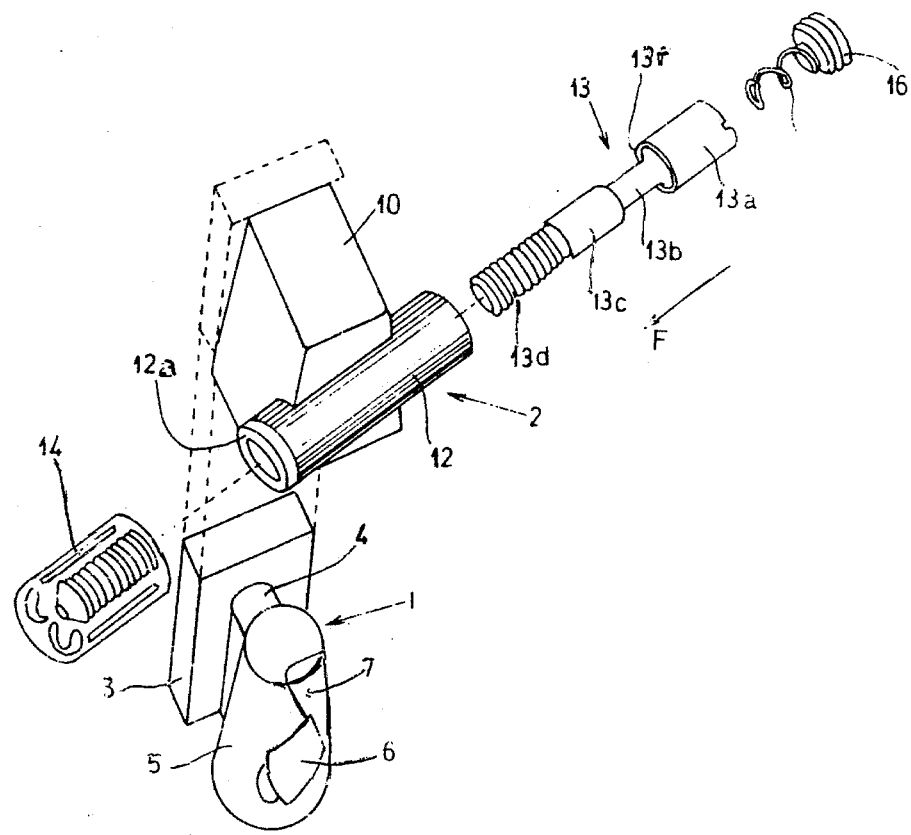

A preferred embodiment of the invention will now be described in detail with reference to the accompanying drawings, in which:

FIG. 1 is a diagrammatic perspective view of natural teeth adjacent to a prosthesis comprising three artificial teeth and provided with connecting apparatus according to the invention, FIG. 2 is a greatly enlarged diagrammatic perspective view of a crown fixed on a natural pillar or stump, with the fixed part of the connecting apparatus secured to this crown, FIG. 3 is a view analogous to FIG. 2, showing in addition the movable part of the connecting apparatus attached to the fixed part, the prosthesis not being shown, FIG. 4 is another large-scale perspective view showing the connecting apparatus, and FIG. 5 is an exploded perspective view of the same elements as shown in FIG. 4, although not in the positions they normally occupy when the connecting apparatus is assembled.

As FIGS. 4 and 5 show most clearly, the dental prosthesis connecting apparatus to be described comprises a male part 1, intended to constitute the fixed part made integral with one of a patient's remaining natural teeth, and a female part 2 forming part of a prosthesis.

Part 1 includes a plate-shaped base 3 used to anchor part 1 on the natural tooth. Plate 3 may, for example, be soldered to a metal crown covering and protecting one of the patient's teeth. Extending from base 3 is a relatively rigid transverse element 4 which supports a frustoconical body 5 constituting the male part proper of the connecting apparatus.

Body 5 is disposed parallel to base 3 and includes on the side remote from base 3 a transverse groove 6 in the shape of a cylindrical segment, the function of which will be described below.

The sidewall of body 5 also includes a second groove 7 running at a slight angle to the vertical axis of frustoconical body 5 and at least partially intercepting groove 6. As can be seen in FIGS. 4 and 5, the groove 6 is a transverse groove having a substantially semi-cylindrical and laterally outwardly open shape. The surface of the groove is generated about a substantially straight line. The function of groove 7 will likewise be explained below.

The female part of this connecting apparatus comprises a block 10 (FIG. 4), within which there is a frustoconical cavity 11, open at the base of the block and matching the frustoconical male part 5. Cavity 11 communicates with the rear surface of block 10 by means of a passage 11' made in this block. The dimensions of passage 11' correspond to those of transverse element 4 of fixed part 1 so that passage 11' can fit over element 4.

Secured to the front face of block 10 is a cylindrical, tubular sleeve 12, within which there is a cylindrical sliding member 13 in the form of a threaded pin. The arrangement of pin 13 will be described below. First it should be explained that the interior of tubular sleeve 12 is formed in such a way as to communicate with frustoconical cavity 11 of block 10 so that when male part 5 is engaged in cavity 11, the surface of groove 6 forms a continuation of that of block 10 and thus constitutes a wall element of cylindrical sleeve 12.

Sliding pin 13 is essentially composed of three sections, the main section 13a having a diameter corresponding to that of the interior of sleeve 12. Following section 13a is a middle section 13b of appreciably smaller diameter. Finally there comes a section 13c, the diameter of which is slightly less than that of section 13a, and which ends in a thread 13d (see FIG. 5).

Sliding pin 13 is inserted into sleeve 12, in the direction indicated by arrow F in FIG. 5, until threaded end 13d projects from the other end of sleeve 12. Terminal section 13c is guided by an annular shoulder 12a having an inside diameter slightly smaller than that of the cylindrical interior of sleeve 12. A tip 14 having an internal thread, used to vary the position of pin 13, is attached to the projecting threaded end 13d. Inserted in the other end of sleeve 12 is a pressure spring 15 which presses against the end face of section 13a of pin 13 and is held in place and biased by a plug 16 screwed into an internal thread of sleeve 12. Thus, spring 15 urges pin 13 axially within sleeve 12 and presses a shoulder 13f, bounding section 13a, against matching shoulder 12a of sleeve 12. In this way, section 13a of sliding pin 13 is held exactly in front of block 10, so that it enters transverse groove 6 of male part 5 when the latter is within cavity 11. The relative positioning of these parts is clearly shown in FIG. 4.

If tip 14 is then pressed in the direction opposite to the biasing action of spring 15, sliding pin 13 moves within sleeve 12 until the smaller-diameter section 13b thereof is in front of cavity 11. The result of this arrangement will be described below.

FIG. 2 shows fixed part 1 with frustoconical male body 5 fixed to a natural tooth D, male part 5 being situated, in this particular case, on the distal side in the area to be occupied by the prosthesis. Part 1 is fixed in a conventional manner, e.g., by soldering base plate 3 of fixed part 1 to the protective cap (crown) covering tooth D, or to a root-anchored cap, or else to a bar.

The female part of the connecting apparatus described will likewise be incorporated in the prosthesis P which is shown in FIG. 1 but not in FIG. 2. In mounting the female part, however, care will be taken to have tip 14, used as the actuating means, still projecting from the prosthesis on the buccal side and consequently accessible.

To attach the prosthesis, as may be seen in FIGS. 1 and 3, cavity 11 fits precisely over male part 5, thus ensuring that the prosthesis is placed in the correct position and completely stabilized. In this attached position, section 13a of sliding pin 13 is so adjusted that it fits partially into cavity 11 and into groove 6 of male part 5, so that this reinforced section 13a acts as a retaining means for the prosthesis and holds it in place in resistance to any force tending to cause upward displacement of the prosthesis.

To detach the prosthesis, it suffices to press on tip 14, thus moving the thinner section 13b of sliding pin 13 back in front of cavity 11, i.e., level with groove 6. In this position, there is nothing more to hold the female part to male part 5 since groove 6 is completely disengaged, so that the prosthesis can be freely lifted upward, i.e., in line with the axis of the corresponding frustoconical fixed and movable parts.

The movement of fitting the prosthesis in place will now be described: it suffices to slip cavity 11 partially over frustoconical body 5, then to press the prosthesis downward. During the course of this movement, shoulder 13f of section 13a of sliding pin 13 enters oblique groove 7, which acts as a ramp and consequently causes pin 13 to move toward the rear end of sleeve 12 against the bias of spring 15 as the female part moves toward the base of the cone and fits on male part 5. When the female part has reached its final position, in which the axis of sliding pin 13 coincides with the axis of cylindrical groove 6, pin 13 is free to move forward, urged by spring 15, and its largest-diameter section 13a engages groove 6 and interlocks the two parts.

In the embodiment described above, cylindrical sleeve 12 with sliding pin 13, and groove 6, are disposed transversely with respect to the vertical axis of the connecting apparatus. However, as shown in FIGS. 3 and 4, it is preferable for these elements to be disposed with their common axis at a slight angle to the horizontal so that tip 14 will be situated as close as possible to the gum and hence be less liable to disturb the patient.

In the preceding description, the terms "upward" and "downward" have been used. These terms relate to use of the apparatus in connecting a prosthesis to a patient's lower jaw teeth. Obviously, however, the terms will be reversed if the connecting apparatus is intended for use with an upper jaw prosthesis.

Furthermore, although in the embodiment described and illustrated, the female part of the connecting apparatus is associated with the prosthesis and the male part with the natural teeth, this arrangement may very well be reversed.

What is claimed is:

1. Connecting apparatus for removable dental prosthesis, of the type having a male part, a female part, and a device for joining said male part and said female part, wherein the improvement comprises:

said male part being of substantially frustoconical shape;

said female part being of substantially frustoconical shape; and said device for joining comprising means for securing said female member to said male member and preventing relative movement therebetween, said means for securing comprising a cylindrical sliding member incorporated in said female part and movable transversely with respect to a longitudinal axis of said female part, said male member having a substantially semi-cylindrical, laterally outwardly open, transverse groove, the surface of which is generated about a substantially straight line, for receiving said sliding member whereby said male part and said female part are interlocked and said sliding member and said transverse groove are coaxial when said sliding member is in place.

2. The apparatus of claim 1, wherein the axis of said sliding member is inclined with respect to a plane perpendicular to the common axis of said male part and said female part.

3. The apparatus of claim 1, wherein said sliding member includes at least a first section and a second section of smaller diameter than said first section, said first section of said sliding member intended to be received in said transverse groove.

4. The apparatus of claim 1, wherein said female part comprises a tubular sleeve made integral therewith, said sliding member being accommodated in said tubular sleeve.

5. The apparatus of claim 4, wherein said tubular sleeve includes internal seating means, further comprising spring means acting along the axis of said tubular sleeve for pressing said sliding member against said seating means.

6. The apparatus of claim 5, further comprising a removable cap fixed to one end of said tubular sleeve for supporting said spring means.

7. The apparatus of claim 1, wherein said male part includes a further groove disposed at a slight angle to the axis of said male part and acting as a guide surface for displacing said sliding member when the prosthesis is being fitted in place.

* * * * *

UNITED STATES PATENT AND TRADEMARK OFFICE
CERTIFICATE OF CORRECTION

PATENT NO. : 4,345,901
DATED : August 24, 1982
INVENTOR(S) : Mario ROMAGNOLI

It is certified that error appears in the above—identified patent and that said Letters Patent is hereby corrected as shown below:

IN THE DESCRIPTION

Column 1, line 36, the word "of" (second occurrence) should be replaced by --or--.

IN THE DRAWINGS

In Fig. 5 the reference number 15 was missing and the upper circular edge of part 5 should have been broken off at the site of the groove 7. (See page 2 of this Certificate.)

UNITED STATES PATENT AND TRADEMARK OFFICE
CERTIFICATE OF CORRECTION

PATENT NO. : 4,345,901

DATED : August 24, 1982

PAGE 2 OF 2

INVENTOR(S) : Mario ROMAGNOLI

It is certified that error appears in the above—identified patent and that said Letters Patent is hereby corrected as shown below:

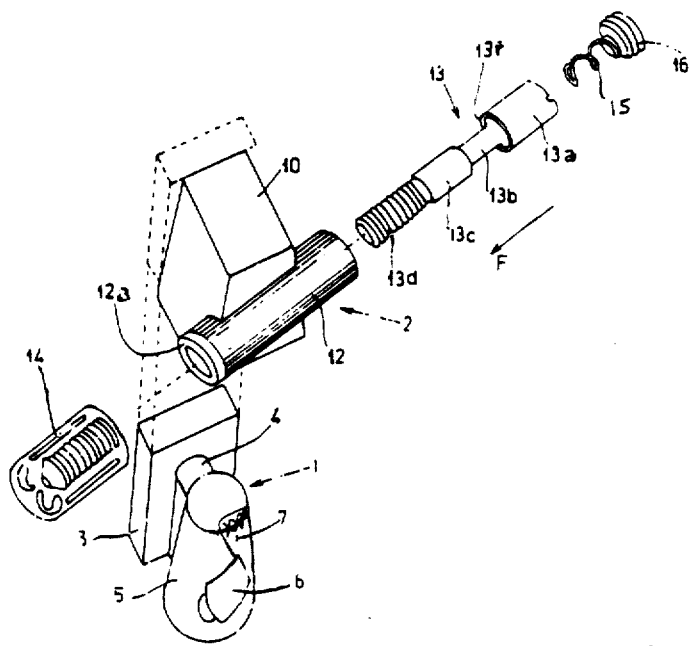

Fig. 5

Signed and Sealed this

Fifth Day of April 1983

[SEAL]

Attest:

GERALD J. MOSSINGHOFF

Attesting Officer    Commissioner of Patents and Trademarks